(12) United States Patent
Jasperse et al.

(10) Patent No.: US 9,658,159 B2
(45) Date of Patent: *May 23, 2017

(54) LIGHT AND SHUTTER FOR A SAMPLE ANALYZER

(71) Applicant: Siemens Healthcare Diagnostics Inc., Tarrytown, NY (US)

(72) Inventors: Jeffrey Jasperse, West Newton, MA (US); Normand Desmarais, Cumberland, RI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 70 days.

This patent is subject to a terminal disclaimer.

(21) Appl. No.: 14/777,664

(22) PCT Filed: Mar. 14, 2014

(86) PCT No.: PCT/US2014/027948
§ 371 (c)(1),
(2) Date: Sep. 16, 2015

(87) PCT Pub. No.: WO2014/152845
PCT Pub. Date: Sep. 25, 2014

(65) Prior Publication Data
US 2016/0109367 A1 Apr. 21, 2016

Related U.S. Application Data

(60) Provisional application No. 61/803,490, filed on Mar. 20, 2013.

(51) Int. Cl.
*G01N 21/76* (2006.01)
*G01N 21/64* (2006.01)

(52) U.S. Cl.
CPC ....... *G01N 21/645* (2013.01); *G01N 21/6486* (2013.01); *G01N 2201/0221* (2013.01); *G01N 2201/062* (2013.01)

(58) Field of Classification Search
CPC ................ G01N 21/76; G01N 21/645; G01N 2021/6463; G01N 2021/6471; G01N 2021/6476
See application file for complete search history.

(56) References Cited

U.S. PATENT DOCUMENTS

| 2,922,349 A | 1/1960 | Rochwite |
| 3,903,528 A | 9/1975 | Kee |

(Continued)

FOREIGN PATENT DOCUMENTS

| CN | 1664689 A | 9/2005 |
| CN | 101266386 A | 9/2008 |

(Continued)

OTHER PUBLICATIONS

European Search Report and Search Opinion of European Application No. 14768894.9 dated on Oct. 31, 2016.

(Continued)

*Primary Examiner* — Nicole Ippolito
*Assistant Examiner* — Sean Luck
(74) *Attorney, Agent, or Firm* — Kyle D. Petaja (57) ABSTRACT

A sample analyzer has a support for an assay sample vessel, a detector, and a shutter assembly. The assay sample vessel contains an assay sample within an assay sample reservoir. The detector has an optical axis aligned with the assay sample reservoir, so as to detect luminescence from the assay sample. The shutter assembly includes an illuminator and is positioned between the detector and the support, intersecting the optical axis, such that the illuminator causes luminescence of the assay sample. Thus both illumination (Continued)

and detection occur on the same side of the assay sample vessel.

19 Claims, 7 Drawing Sheets

(56) References Cited

U.S. PATENT DOCUMENTS

| | | | |
|---|---|---|---|
| 3,918,077 A | 11/1975 | Burton et al. | |
| 3,928,859 A | 12/1975 | Peterson | |
| 4,007,469 A | 2/1977 | Land et al. | |
| 4,112,450 A | 9/1978 | Kondo | |
| 4,515,445 A * | 5/1985 | Muller | G02B 21/088 359/386 |
| 4,827,348 A | 5/1989 | Ernest et al. | |
| 4,978,991 A | 12/1990 | Farrington | |
| 5,408,363 A | 4/1995 | Kano | |
| 5,709,994 A | 1/1998 | Pease et al. | |
| 5,833,924 A | 11/1998 | McClintock et al. | |
| 6,139,153 A | 10/2000 | Alscher et al. | |
| 6,313,471 B1 | 11/2001 | Giebeler et al. | |
| 6,466,353 B2 | 10/2002 | Tuchman | |
| 6,495,373 B1 | 12/2002 | Mauchan | |
| 6,850,351 B1 | 2/2005 | Djachiachvili | |
| 7,402,281 B2 | 7/2008 | Huynh-Ba et al. | |
| 2003/0044967 A1* | 3/2003 | Heffelfinger | G01J 3/14 435/287.2 |
| 2003/0137725 A1* | 7/2003 | Mueller | G02B 21/088 359/386 |
| 2004/0178370 A1* | 9/2004 | Oldham | G01J 3/10 250/559.4 |
| 2006/0158666 A1* | 7/2006 | Schelinski | G01B 11/24 356/614 |
| 2007/0177049 A1 | 8/2007 | Kreysar et al. | |
| 2008/0090198 A1* | 4/2008 | Liang | A61B 1/0638 433/29 |
| 2008/0129736 A1 | 6/2008 | Sun et al. | |
| 2009/0153956 A1* | 6/2009 | Kusaka | G02B 21/08 359/385 |
| 2009/0225407 A1* | 9/2009 | Nakayama | G02B 21/16 359/370 |
| 2010/0024526 A1 | 2/2010 | Colvin, Jr. et al. | |
| 2010/0142038 A1* | 6/2010 | Sugiura | G02B 21/082 359/381 |
| 2010/0276605 A1 | 11/2010 | Olsen et al. | |
| 2011/0007312 A1 | 1/2011 | Bushaw et al. | |
| 2011/0049385 A1* | 3/2011 | Laitinen | G01J 3/02 250/458.1 |
| 2011/0102888 A1* | 5/2011 | Honda | G02B 21/06 359/385 |
| 2012/0231493 A1 | 9/2012 | Noda et al. | |

FOREIGN PATENT DOCUMENTS

| | | |
|---|---|---|
| EP | 0325410 A1 | 9/1989 |
| GB | 456617 A | 11/1936 |
| JP | H05-90457 U | 12/1993 |
| JP | 2004348051 A | 12/2004 |
| WO | 2009111834 A1 | 9/2009 |
| WO | 2013181052 A1 | 12/2013 |

OTHER PUBLICATIONS

Supplemental Partial European Search Report of European Application No. 13798044 (Attorney Docket No. 2011P23597WE) dated Apr. 1, 2016.

International Search Report and Written Opinion of International Application No. PCT/US2014/027948 dated on Jul. 18, 2014.

* cited by examiner

LIGHT AND SHUTTER FOR A SAMPLE ANALYZER

This application is the US National Stage of International Application No. PCT/US2014/027948, filed Mar. 14, 2014 and claims the benefit thereof. The International Application claims the benefit of U.S. Provisional Application No. 61/803,490, filed Mar. 20, 2013. All of the applications are incorporated by reference herein in their entirety.

This application claims benefit of provisional application U.S. Ser. No. 61/803,490, filed Mar. 20, 2013. The entire contents of the before-referenced application are expressly incorporated herein by reference.

BACKGROUND OF THE INVENTIVE CONCEPTS

1. Field of the Inventive Concepts

The inventive concepts disclosed and claimed herein relate generally to luminescence-based analyzers, and more particularly, but not by way of limitation, to a luminescence-based analyzer having a shutter and illuminator assembly allowing both illumination and detection from the same side of an assay sample vessel.

2. Brief Description of Related Art

Analytical instrumentation utilizing luminescence detection is heavily utilized in the pharmaceutical and medical industries. Analytical measurements are often performed using a beam of catalyzing radiation to interact with a specific sample-reagent combination. The resulting photon emission, often very weak, is then detected and measured with a sensitive detector, converted to an electrical signal, and further correlated to provide the actual analytical result.

For example, U.S. Pat. No. 5,709,994 discloses a highly sensitive method of assaying known as a Luminescent Oxygen Channeled. Immunoassay (LOCI). The method uses a photosensitizer that generates singlet oxygen upon irradiation, and a chemiluminescent compound that is activated by the singlet oxygen. The photosensitizer and the chemiluminescent compound are irradiated with light of a certain wavelength, after which the resulting light emitted by the chemiluminescent compound is measured and correlated to provide the assay.

The instrumentation utilized for luminescence-based assays is often physically large due, in part, to the intricate and sensitive optics used. The analyses often involve exposure of the sample, such as one contained in a microfluidic card, to a high intensity light in order to activate, for example, LOCI sensibeads. The resulting photon emission, often very weak, is then detected and measured with a sensitive detector such as a photomultiplier tube, converted to an electrical signal, and further correlated to provide the actual analytical result. Existing analyzers illuminate a sample in a microfluidic card from one side or the card, and the detection system is on the opposite side of the card. To protect the sensitive detector, it is common to widely separate the detector from the high intensity light source and to provide path barriers and shutters between the two.

Size is not a major concern in large laboratories facilitating high-throughput screening; however, it would be useful to have a lighter, portable unit or handheld device capable of producing accurate luminescence-based analyses. One approach for smaller units to achieve the proper illumination intensity without harming the detector is to utilize multiple illumination sources focused away from the detection optical axis. However, use of multiple illumination sources requires multiple access points to the assay vessel.

In view of the foregoing, there is a need for a luminescence-based sample analyzer that provides both sample illumination activation and sensitive luminescence detection from a single sample access point, while still protecting the sensitive detector. It is to such a compact and energy-efficient design that the presently disclosed and claimed inventive concept(s) is directed.

SUMMARY OF THE INVENTIVE CONCEPTS

The inventive concepts disclosed and claimed herein generally relate to a sample analyzer utilizing luminescence. The sample analyzer has a support for an assay sample vessel, a detector, and a shutter assembly. The assay sample vessel contains an assay sample within an assay sample reservoir. The detector has an optical axis aligned with the assay sample reservoir, so as to detect luminescence from the assay sample. The shutter assembly includes an Illuminator and is positioned between the detector and the support, intersecting the optical axis, such that the illuminator causes luminescence of the assay sample.

In one embodiment, the shutter assembly has a first shutter blade with a first light transmitting aperture therein and the illuminator thereon; and a second shutter blade positioned adjacent and parallel to the first shutter blade. The second shutter blade has a second light transmitting aperture therein. The first and second shutter blades are supported to allow parallel linear motion and are moveable linearly in opposite directions between an open measuring position and a closed illumination position. In the open measuring position, the first and second light transmitting apertures are in an overlapping relationship with respect to one another. In the closed illumination position, the first and second light transmitting apertures are in a non-overlapping relationship with respect to one another and the Illuminator is proximate the assay sample reservoir such that the illuminator causes luminescence of the assay sample.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily the scale and certain features and certain views of the figures may be shown exaggerated, to scale or in schematic in the interest of clarity and conciseness. In the drawings.

DETAILED DESCRIPTION OF EXEMPLARY EMBODIMENTS

Before explaining at least one embodiment of the inventive concept disclosed herein in detail, it is to be understood that the inventive concept is not limited in its application to the details of construction, experiments, exemplary data, and/or the arrangement of the components set forth in the following description, or illustrated in the drawings. The presently disclosed and claimed inventive concept is capable of other embodiments or of being practiced or carried out in various ways. Also, it is to be understood that the phraseology and terminology employed herein is for purpose of description only and should not be regarded as limiting in any way.

In the following detailed description of embodiments of the inventive concept, numerous specific details are set forth in order to provide a more thorough understanding of the inventive concept. However, it will be apparent to one of ordinary skill in the art that the inventive concept within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless it is obvious that it is meant otherwise.

References to the Luminescent Oxygen Channeling immunoassay (LOCI) methods and optical systems are for example only, and the inventive concepts can be used with any sample analysis procedure utilizing luminescence, detection. Reference to a "sample" or "assay sample" refers to the sample to be analyzed and includes reagents added according to the analysis procedure, those reagents added either before or after insertion into the assay sample vessel.

Finally, as used herein any reference to "one embodiment" or "an embodiment" means that a particular element, feature, structure, or characteristic descibed in connection with the embodiment is included in at least one embodiment. The appearances of the phrase "in one embodiment" in various places in the specification are not necessarily all referring to the same embodiment.

Techniques utilizing chemiluminescence have been used to diagnose a great variety of analytes and samples in applications ranging from drug analysis to soil analysis and food chemistry. Liquid phase chemiluminescent analyses include enzyme assays and assays for carbohydrates, nucleotides, steroids and various drugs. As discussed in U.S. Pat. No. 7,402,281, various types of analytical tests related to patient diagnosis and therapy can be performed by analysis of a liquid sample taken from a patient's infections, bodily fluids or abscesses. Examples of bodily fluids include urine, blood serum, plasma, saliva, cerebrospinal fluid and the like.

An "immunoassay" measures the presence or concentration of an analyte such as a hormone or enzyme based on its ability to act as an antigen or antibody in a chemical reaction. Chemiluminescent immunoassays utilize a chemiluminescent label that produces light when excited by chemical energy, usually coming from an oxidation-reduction reaction. The chemiluminescent molecules can be conjugated directly to antigens, or they can be used as substrates for enzyme labels. Commonly used chemiluminescent labels include acrodinium, luminol, and dioxetane.

A LOCI technique can be used to assay very small samples of plasma and is based on the proximity of two different coated synthetic particles or beads, a sensitizer bead containing a photosensitizer, and a chemiluminescer bead containing a chemiluminescer. In one LOCI procedure, streptavidin is bound to the surface of the sensitizer bead where it can absorb light at 680 nm to generate singlet oxygen. This allows use of commercially available 680 nm solid state laser or diodes for excitation. The chemiluminescer bead is coated with an analyte-specific antibody. Analyte in the sample binds to the analyte-specific antibody on a chemiluminescer bead and also binds to a biotinylated receptor reagent linked to a streptavidin on the sensitizer bead. The analyte thus causes formation of a particle dimer, i.e., the sensitizer bead linked with the chemiluminescer bead. The chemiluminescer bead contains an olefin dye (thioxene) which reacts with singlet oxygen, releasing chemiluminescence at 390 nm. The short half life of the singlet oxygen ensures that the sensitizer bead must be in very close contact with the chemiluminescer bead to generate the chemiluminescence. Thus, creation of a particle dimer allows generation a chemiluminescent signal, while unassociated particles cannot generate chemiluminescent signals. A fluorescent energy acceptor immediately shifts the emission wavelength to 612 nm, and the resulting light emission directly correlates with the amount of particle pairs or dimers, allowing quantification of the concentration of analyte in the sample.

Figure 1:
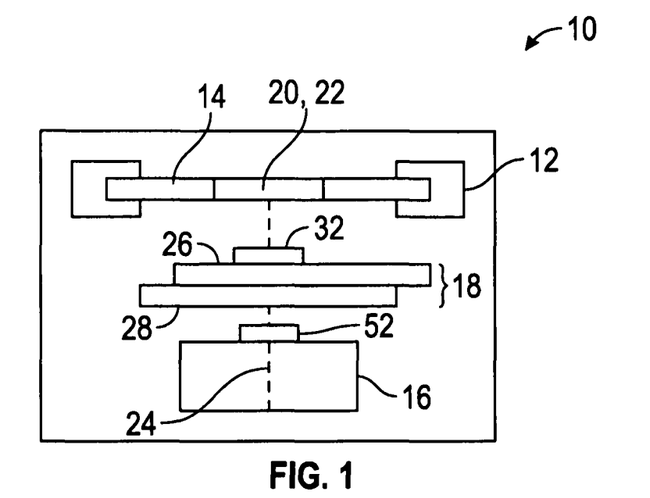
FIG. 1 is a schematic representation of an embodiment of a sample analyzer constructed in accordance with the Inventive concepts disclosed herein.

Referring now to the drawings, and more particularly to FIG. 1, shown therein is an exemplary embodiment of a sample analyzer 10 constructed in accordance with the inventive concepts disclosed and claimed herein. The sample analyzer 10 has a support 12 for an assay sample vessel 14, a detector 16, and a shutter assembly 18. The assay sample vessel 14 holds an assay sample 20 within a sample reservoir 22. The detector 16 has an optical axis 24 aligned with the sample reservoir 22, so as to detect luminescence emitted from the assay sample 20. The shutter assembly 18 is positioned between the detector 16 and the support 12, intersecting the optical axis 24. This configuration of the sample analyzer 10 allows for both illumination and luminescence detection from the same side of the sample reservoir 22, offering numerous benefits as described in detail hereinafter.

Figure 2:
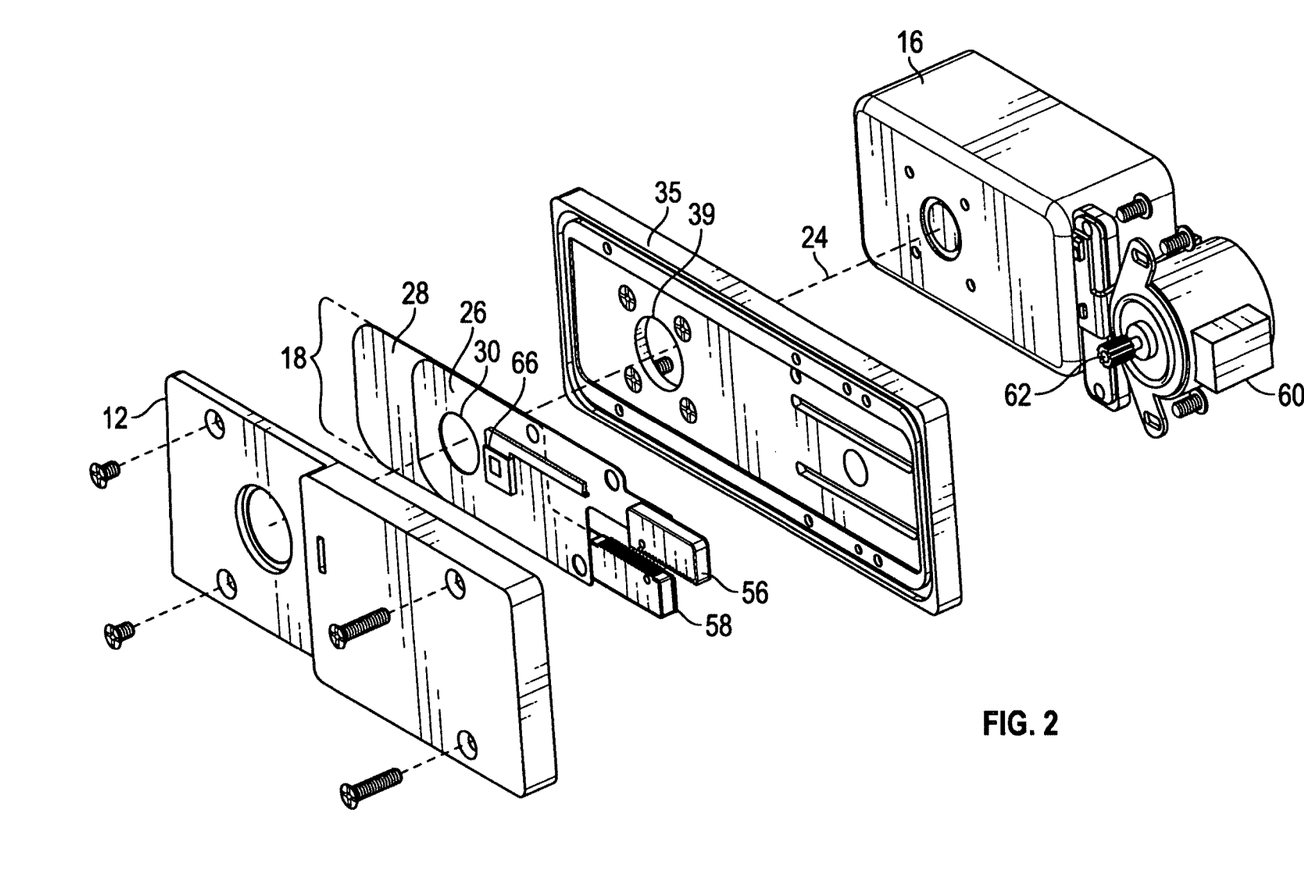
FIG. 2 is an exploded view of another embodiment of a sample analyzer.
Figure 3:
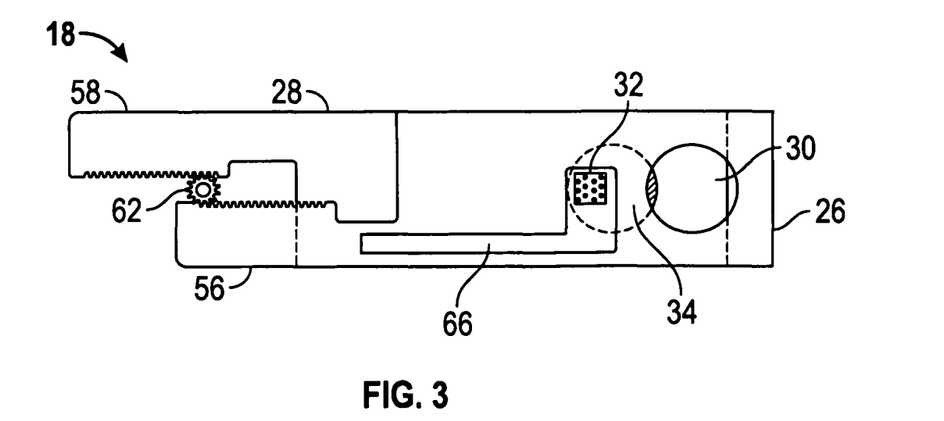
FIG. 3 is a schematic representation of an embodiment of a shutter assembly constructed in accordance with the inventive concepts disclosed herein.
Figure 4A:
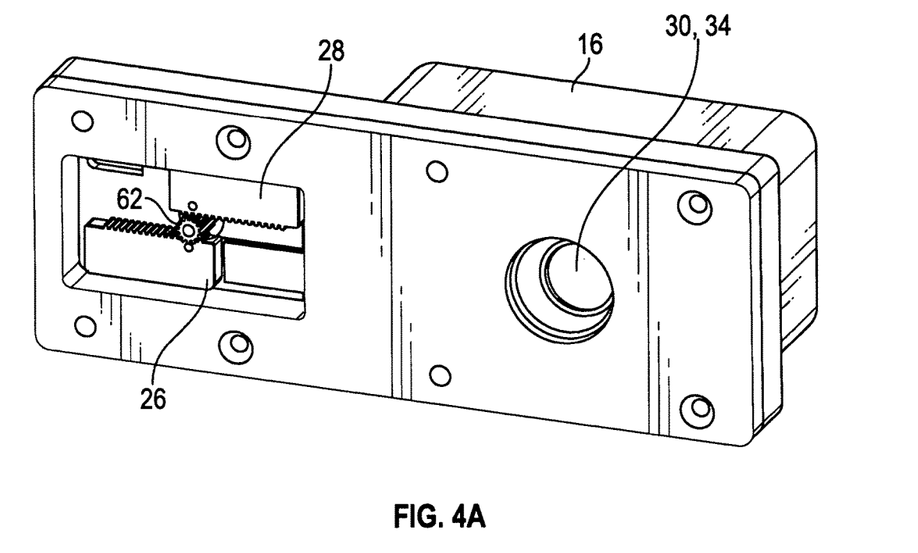
FIG. 4A-FIG. 4B provide a schematic representation of a shutter assembly embodiment in an open measuring position.
Figure 4B:
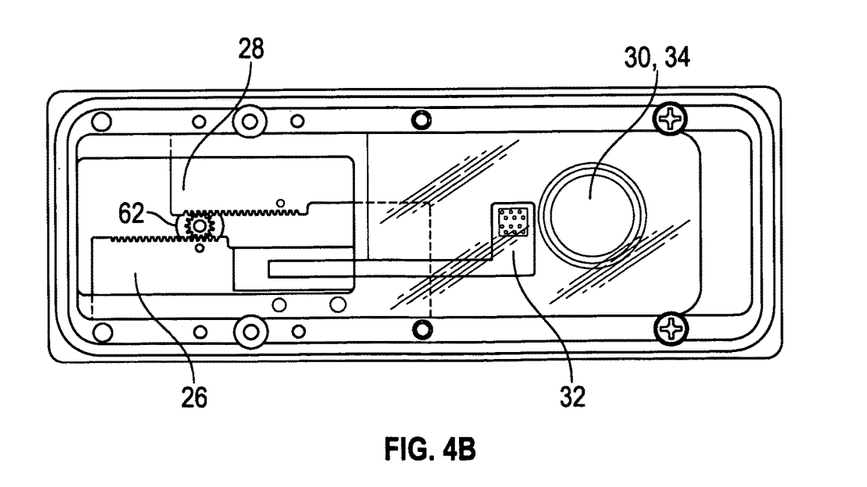
Figure 5A:
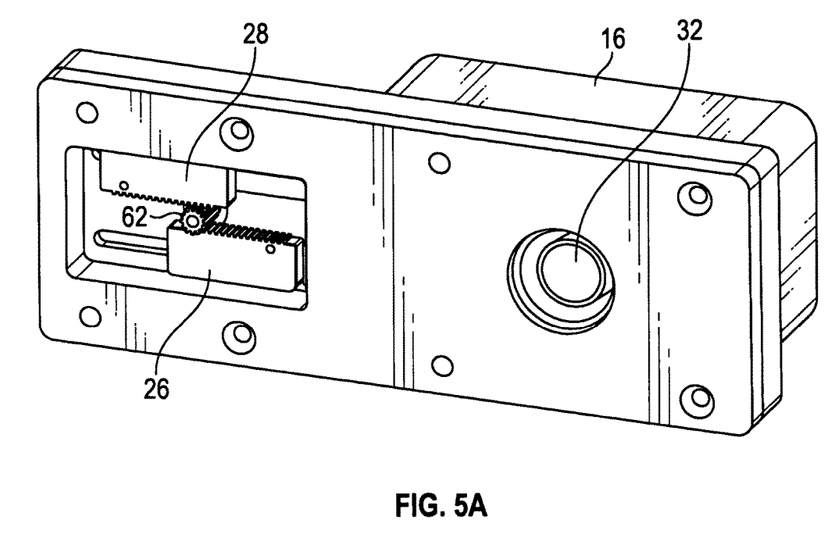
FIG. 5A-FIG. 5B provide a schematic representation of a shutter assembly embodiment in a closed illumination position.
Figure 5B:
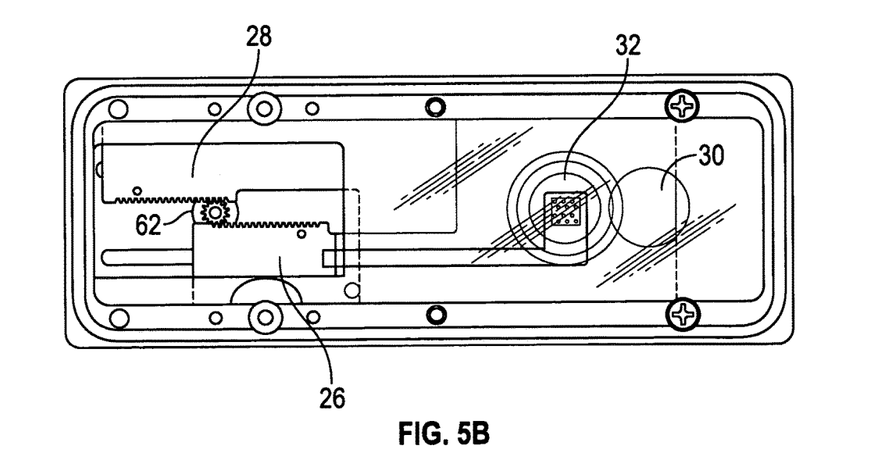

Referring now to FIG. 2, in one embodiment the shutter assembly 18 has a first shutter blade 20 and a second shutter blade 28 positioned adjacent and parallel to the first shutter blade 26. The first shutter blade 26, shown in more detail in FIG. 3, has a first light transmitting aperture 30 therein, and an illuminator 32 thereon. The second shutter blade 28 has a second light transmitting aperture 34 therein. The first and second shutter blades, 26 and 28 respectively, are supported to allow parallel linear motion and are moveable linearly in opposite directions between an open measuring position and a closed illumination position. In one embodiment, the shutter assembly is sandwiched between the support 12 and a shutter blade guide plate 35 having a light transmitting aperture 39 positioned along the optical axis 24. In the open measuring position shown in FIGS. 4A and 48, the first and second light transmitting apertures, 30 and 34 respectively, are in an overlapping relationship with respect to one another, allowing luminescence from the assay sample 20 to reach the detector 16. In the closed illumination position shown in FIGS. 5A and 58, the first and second light transmitting apertures, 30 and 34 respectively, are in a non-overlapping relationship with respect to one another, thereby protecting the detector 16. In this closed illumination position, the illuminator 32 is proximate the sample reservoir 22 to cause luminescence of the assay sample 20, but unlike previous analyzer designs, the illumination is directed away from the detector 16.

The basic sample analysis process includes insertion of a liquid to be assayed into an assay sample vessel; irradiation (sometimes referred to hereinafter as "illumination") of the assay sample to cause the sample to luminesce; detection of the light emitted by the sample as a result of the irradiation or illumination; and correlation of the amount of detected light to the assay. Various types and configurations of assay sample vessels 14 can be used. In one embodiment, the assay sample vessel 14 is a microfluidic "card" having a disk-shaped assay sample reservoir 22.

Figure 6:
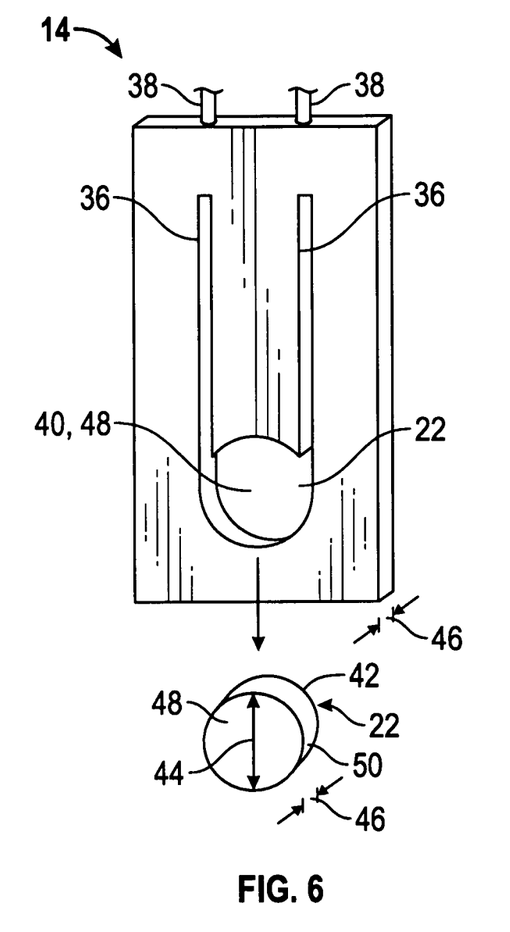
FIG. 6 is a schematic representation of an embodiment of a microfluidic card sample vessel constructed in accordance with the inventive concepts disclosed herein.

A simplified model of a microfluidic card is shown in FIG. 6. The model in FIG. 6 includes only the sample reservoir 22, fluid feeds 36 and fluid inlets 38. The sample reservoir 22 is shown as a circular or disc shaped feature toward the bottom of the card. An assay sample 20 can be delivered to the sample reservoir 22 through fluid feeds 38 by injecting the assay sample 20 into one of the fluid inlets 38. An accessible side 40 of the sample reservoir 22 is transparent to light from the illuminator 32 and to luminescent light from the assay sample 20, while the back face 42 does not require sample accessibility. Such sample vessel design allows for a relatively thin sample reservoir 22 having a large diameter 44 relative to the thickness 46 of the sample reservoir 22. The thin sample reservoir 22 provides a large surface area for an illuminating and measuring face 48 relative to the surface area of an edge 50.

The illuminator 32 can be multi-wavelength, optionally filtered to cut off undesired wavelengths, or can be a laser providing monochromatic light. Light intensity and time of irradiation may vary widely. In one embodiment, a light emitting diode (LED) is used. In another embodiment, the illuminator 32 comprises two or more LEDs, hereinafter referred to as an LED array. For example, in one embodiment a 12-die LED array is used having 80 mA/die providing reliability, intensity falloff over time and wavelength stability. In another embodiment, a 20 to 24 die LED array in a flat no-lead surface mount package is used.

Figure 8:
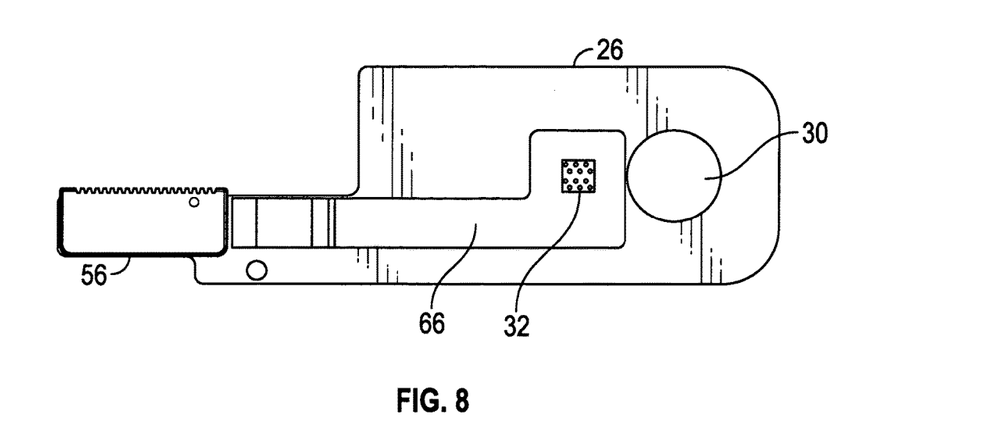
FIG. 8 is a schematic representation of a first shutter blade including a diode array on a flex circuit.
Figure 9:
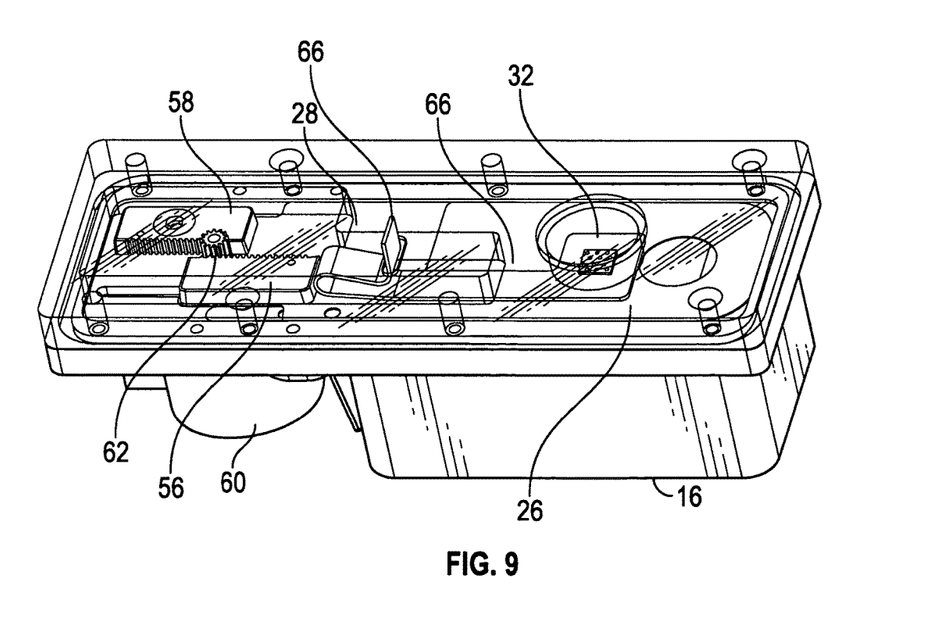
FIG. 9 depicts an embodiment of a sample analyzer constructed in accordance with the inventive concepts disclosed herein.

In one embodiment, the illuminator 32 is provided on a flex circuit 66. Flexible printed circuit boards, referred to herein as flex circuits, make use of technology for assembling electronic circuits by mounting or screen printing electronic devices onto flexible plastic substrates. Flex circuit technology is well known by those skilled in the art. The flex circuit 66 is attached to the first shutter blade 26 using an adhesive or other means known to those skilled in the art.

The detector 16 can be any known or yet to be developed photo-detector having a sensitivity required by the particular assay. For example, vacuum photodetectors such as photomultiplier tubes (PMTs) are typically very sensitive compared to solid state photodetectors such as silicon photodiodes. Photodetectors and their use are well known to those skilled in the art. The detector 16, using photon-counting electronics, measures light emission from the assay sample 20 over a defined time interval, typically around 10 seconds. The analyte concentration in the assay sample 20 is directly proportional to the assay sample volume and the photon production. Sample analyzer software computes the analyte concentration from the photon count. During manufacture, the sample analyzer 10 can be calibrated using a set of standards of known analyte concentration to insure accurate assay reporting.

Figure 7A:
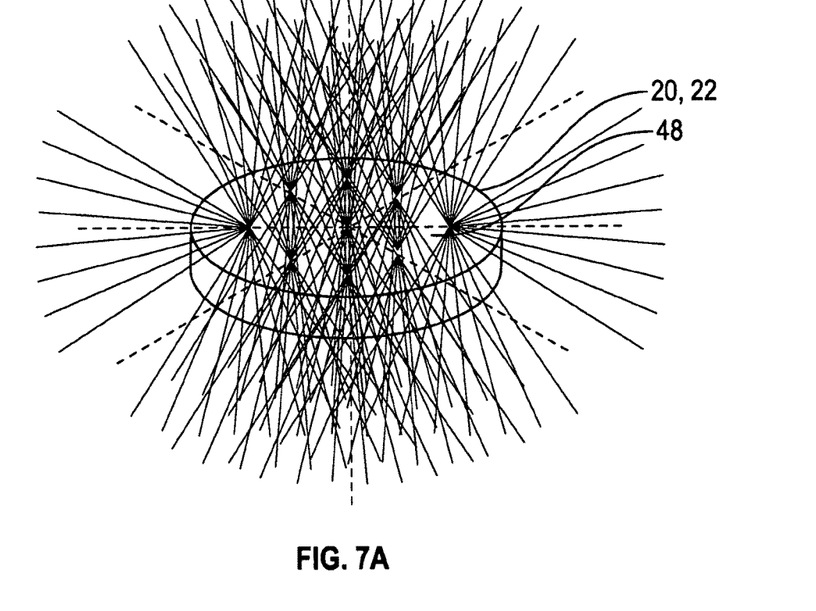
FIG. 7A is a model of light emitted by a luminescent sample in a disc shaped sample reservoir.

FIG. 7A shows modeling results of photon emission from a luminescent assay sample within a disc shaped sample reservoir 22. The photon emission pattern from the assay sample in the sample reservoir 22 is isotropic. Some photons emerge towards the detector 16 and some emerge away from it. As a consequence, emerging photons not incident to detector intake optics 52 can be lost by scatter and absorption effects in the surrounding infrastructure, resulting in reaction relevant photons not being counted.

Figure 7B:
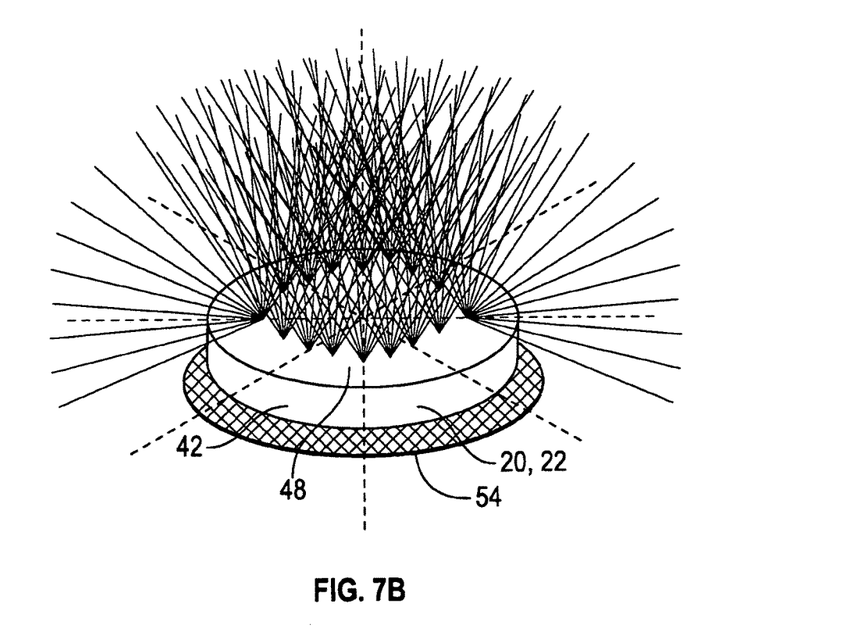
FIG. 7B is a model of light emitted by a luminescent sample in a disc shaped sample reservoir having a reflector adjacent one side.

FIG. 7B shows modeling results of photon emission from a luminescent assay sample within a disc shaped sample reservoir 22 having a permanent reflector 54 adjacent the back face 42 of the sample reservoir 22. Photons that emerge from the assay sample in a direction away from the detector 16 are now reflected off the permanent reflector 54, back through the assay sample 20, and out the illuminating and measuring face 48 of the sample reservoir 22. More of the photons are directed toward the detector 16, and measurement of photon emission is significantly improved.

Similar use of a reflector was recently described for a sample analyzer designed to sandwich a microfluidic card between the illuminator and the detector. The reflector was used to reflect the sample luminescence to improve measurement of photon emission, and it was shuttled out of the way in order to illuminate the assay sample. Embodiments of the presently disclosed inventive concepts utilize a single illuminating and measuring face 48, allowing the permanent reflector 54 to be in a fixed position. The terms "permanent reflector" and "permanently mounted" are used herein to mean that the reflector remains in the same position during both the illumination and the detection cycles of a sample analysis, rather than being shuttled away for one of the cycles.

The permanent reflector 54 can be located in the sample analyzer 10, or it can be integrated into the assay sample vessel 14 itself. In one embodiment, the back face 42 of the sample reservoir 22 has a reflective surface. In another embodiment, a permanent reflector 54 is provided on a wall (not shown) of the sample analyzer 10 adjacent a transparent back face 42 of the sample reservoir 22 when the assay sample vessel 14 is inserted for analysis. The permanent reflector 54 can be flat or curved and can include any material having suitable reflective properties. Two example reflectors tested were a commercially available 1 mm thick flat mirror and a custom parabolic spline reflector. The parabolic reflector can be manufactured using a vacuum deposition process over a plastic form. Tests with the flat mirror reflector showed a measured improvement in signal gain of 1.5 times compared to the measurement without the reflector. Tests with the parabolic reflector showed a signal gain of 2 times that obtained without the reflector. Use of the permanent reflector 54 not only improves the photon signal harvesting, i.e., detection of the light emitted by the sample as a result of the illumination, but by reflecting light back through the sample during the illumination stage, the illumination penetration of the assay sample is also improved.

In one embodiment, the sample reservoir 22 includes an air space to mitigate bubble volume loss from the assay sample 20. This air space would necessarily interfere with either the illumination or the detection mode in an apparatus having the assay sample vessel 14 sandwiched between the detector 16 and the illuminator 32. However, utilizing the inventive concepts presently disclosed, the detector 16 and the illuminator 32 can both be positioned under the assay sample vessel 14, allowing bubbles to rise away from the illuminating and measuring face 48, such that there is no interference with either the illumination or the detection steps.

The shutter assembly 18 operates to maintain the first and second light transmitting apertures 30 and 34, respectively, in a closed, non-overlapping position during the illumination interval, thereby blocking light, transmission from the illuminator 32 to the detector 16 and protecting the detector 16 from over exposure. During the illumination interval, the illuminator 32 is adjacent the sample reservoir 22 and shines light into the assay sample 20 thereby activating the assay sample 20 to start the reaction and photon emission. After the illumination interval, the assay sample 20 begins to respond by emitting photons which are counted by the detector 16. In the measuring mode, the illuminator 32 is fully retracted from the sample reservoir 22 and the shutter assembly 18 operates to maintain the first and second light transmitting apertures 30 and 34, respectively, in an open, overlapping position to allow light emitted by the assay sample to enter and be measured by the detector 16. It was found that by having the illuminator 32 fully retracted from the sample reservoir 22 before reading the assay signal, interference caused by a characteristic after-glow of many LED-type illuminators can be nearly eliminated.

Referring back to FIG. 3, in one embodiment the first shutter blade 26 is planar in shape with a first toothed arm 56 extending therefrom. The illuminator 32 comprises a diode array, positioned on the first shutter blade 26 and aligned with the first light transmitting aperture 30. The second shutter blade 28 is also planar in shape with a second toothed arm 58 extending therefrom. The second shutter blade 28 is positioned adjacent and parallel to the first shutter blade 26, and both shutter blades 26 and 28 are slideably supported on the shutter assembly 18 to allow parallel linear motion.

The first and second shutter blades 26 and 28 are typically shaped as thin metal blades with dimensions determined, in large part, by the sizes of the sample reservoir 22 and the detector 16. Suitable construction can include any rigid material that is impervious to light. A variety of suitable metal alloys and polymers are known to those skilled in the art and are readily available commercially.

The shutter assembly 18 is operated by an actuator mechanism to cause the first and second shutter blades 26 and 28, respectively, to move linearly in opposite directions between an open measuring position in which the first and second light transmitting apertures 30 and 34 are in an overlapping relationship with respect to one another, and a closed illumination position in which the first and second light transmitting apertures 30 and 34 are in a non-overlapping relationship with respect to one another and the illuminator 32 on the first shutter blade 26 is proximate the sample reservoir 22. In this position the illuminator 32 causes luminescence of the assay sample 20 with little or no exposure of the detector 16. Non-limiting examples of a suitable shutter actuator mechanism include a motor and solenoid with linkage to the shutter working against a spring, and a stepper motor.

A spring (not shown) or the like may be used to urge the first and second shutter blades 26 and 28 into a closed position to protect the detector 16. Shutters, such as those used in cameras and laboratory instrumentation utilizing luminescence detection, are commonly controlled using a solenoid working against a spring. The solenoid requires continued power input to work against the spring or the like to maintain the shutter in an open position. The analytical instruments requiring shutters are usually powered by AC current, and the solenoid power requirements are not a major concern. Battery power drain is not significant with camera shutters because the shutter typically does not remain open for long periods. However, because of the relatively long time the shutter must remain open in luminescence-based sample analyzers, the power required for operation of a solenoid-controlled shutter in a battery-operated luminescence-based sample analyzer is significant.

In one embodiment, a motor 60, attached to the shutter assembly 18, provides a gear 62 which is disposed between, and meshed with, the first and second toothed arms 56 and 58, respectively. Rotation of the gear 62 causes the first and second shutter blades 26 and 28, respectively, to move linearly in opposite directions between the open measuring position and the closed illumination position.

In one embodiment, the motor 60 is a stepper motor. A stepper motor is a brushless, electric motor having a number of "toothed" electromagnets arranged around a central gear-shaped bar of iron, each electromagnet providing a "step." A full rotation is thus divided into a number of individual steps, and the motors position can be precisely controlled without requiring a feedback mechanism. As the speed of the stepper motor increases, torque decreases. The maximum torque occurs when the motor is stationary, and this "holding torque" determines the ability of the motor to maintain a desired position under external load. Thus, the stepper motor 60 advantageously provides a holding torque which can be used to maintain the shutter blades in a precisely controlled position, whether closed, full open, or any position between. Because the stepper motor 60 requires no power to maintain a shutter position, it reduces the power requirements of a portable luminescence-based analyzer making such battery powered devices practical.

Additionally, the time taken for the stepper motor 60 to open the first and second shutter blades 28 and 28, respectively, is fast, due in part because the mass of the shutter blades and resulting inertia is small, and because the stepper motor 60 can be run at its highest velocity, sometimes called "high speed slewing." Thus, the shutter assembly 18 utilizing the stepper motor 60 can be used to control the exposure time of the detector 16 in addition to protecting the detector 16 from light from the illuminator 32.

In one prototype, the first and second shutter blades 26 and 28 were constructed of 0.127 mm thick 304 stainless steel. This material is readily available and provided a high degree of light blocking. The gear-tooth racks on the first and second toothed arms 58 and 58, respectively, were constructed by over-molding. The over-molding provides a low-cost method to make the teeth compared to cutting the metal blades by, for example, electrical discharge machining (EDM). The over-mold can be made significantly thicker than the blades to provide a greater surface contacting the gear 62. Additionally, use of a plastic over-mold having plastic teeth meshing with metal gear teeth provides a very robust interface. The prototype blades were treated with a black oxide coating to prevent photon tunneling and reflections; however, use of the coating is optional and not critical.

The friction caused between the blades is low, thereby providing a low torque requirement and allowing high speed operation. This allows a more compact design and reduced power requirements compared to existing laboratory luminescence-based sample analyzers. For example, in one embodiment, the detector 16 is positioned about 10 mm or less from the assay sample 20. In another embodiment the detector 16 is positioned about 6 mm or less from the assay sample 20. This is significantly more compact than present bench scale sample analyzers wherein the distance between the detector and the assay sample is on the order of 80 mm or more. This is a significant achievement, particularly in embodiments utilizing a photomultiplier tube. Such compaction provides embodiments wherein the sample analyzer 10 is portable and/or hand-held and can be operated using a power supply (not shown) consisting of one or more batteries.

From the above description, it is clear that the inventive concept(s) disclosed herein is well adapted to carry out the objects and to attain the advantages mentioned herein as well as those inherent in the inventive concept(s) disclosed herein. While exemplary embodiments of the inventive concept(s) disclosed herein have been described for purposes of this disclosure, it will be understood that numerous changes may be made which will readily suggest themselves to those skilled in the art and which are accomplished without departing from the scope of the Inventive concept(s) disclosed herein and defined by the appended claims.

What is claimed is:

1. A sample analyzer, comprising:
   a support for an assay sample vessel containing an assay sample within a sample reservoir;
   a detector having an optical axis aligned with the sample reservoir, so as to detect a luminescence of the assay sample; and
   a shutter assembly, the shutter assembly intersecting the optical axis and positioned between the detector and the support, the shutter assembly comprising a first shutter blade, a second shutter blade, a motor, and an illuminator,
   the first shutter blade and the second shutter blade having a first light transmitting aperture and a second light transmitting aperture, respectively;
   the motor causing the first shutter blade and the second shutter blade to move between an overlapping relationship with respect to one another along the optical axis, and a closed position in which the first and second light transmitting apertures are in a non-overlapping relationship with respect to one another along the optical axis;
   the illuminator being disposed on the first shutter blade adjacent to the first light transmitting aperture;
   the motor causing the first shutter blade and the second shutter blade to move between an illumination position and a measuring position, while in the illumination position: (1) the illuminator is proximate to and aligned with the sample reservoir along the optical axis and (2) the first shutter blade and the second shutter blade are in the closed position, while in the measuring position: (1) the illuminator is offset from the optical axis and (2) the first shutter blade and the second shutter blade are in the open position;
   the illuminator illuminating the assay sample while the first shutter blade and the second shutter blade are in the illumination position;
   the detector detecting luminescence of the assay sample while the first shutter blade and the second shutter blade are in the measuring position.

2. The sample analyzer of claim 1, further comprising a reflector permanently mounted proximate a back face of the sample reservoir, aligned with and perpendicular to the optical axis, to reflect light from the illuminator back into the assay sample in an illumination mode and to reflect a portion of the luminescence back through the assay sample toward the detector in a measuring mode.

3. The sample analyzer of claim 2, wherein the reflector is a flat mirror.

4. The sample analyzer of claim 2, wherein the reflector is a parabolic conic reflector.

5. The sample analyzer of claim 1, wherein the sample reservoir includes a reflector on a back face of the sample reservoir, aligned with and perpendicular to the optical axis, such that the reflector reflects light from the illuminator back into the assay sample in an illumination mode, and reflects a portion of the luminescence back through the assay sample toward the detector in a measuring mode.

6. The sample analyzer of claim 1, wherein the assay sample is positionable above the detector, such that one or more gas bubbles present in the assay sample will rise away from both the illuminator and the detector.

7. The sample analyzer of claim 1, wherein the illuminator comprises a light emitting diode (LED) or an LED array mounted on a flexible circuit attached to the first shutter blade.

8. The sample analyzer of claim 1, further comprising:
   a first toothed arm extending from the first shutter blade;
   a second toothed arm extending from the second shutter blade; and
   a motor having a gear disposed between, and meshed with, the first and second toothed arms such that rotation of the gear causes the first and second shutter blades to move linearly in opposite directions between the measuring position and the illumination position.

9. The sample analyzer of claim 8, wherein the detector is positioned less than 10 mm from the assay sample.

10. The sample analyzer of claim 8, wherein the motor and gear provide a direct drive mechanism.

11. A method of analyzing as assay sample, comprising:
   operating a sample analyzer comprising:
      a support for an assay sample vessel having a sample reservoir containing an assay sample;
      a detector having an optical axis aligned with the assay sample reservoir, so as to detect a luminescence of the assay sample;
      a shutter assembly positioned between the detector and the support and intersecting the optical axis, the shutter assembly having:
         a first shutter blade with a first light transmitting aperture therein and an illuminator thereon; and
         a second shutter blade positioned adjacent and parallel to the first shutter blade, the second shutter blade having a second light transmitting aperture therein, the first and second shutter blades supported to allow parallel linear motion;
      wherein the first and second shutter blades are moveable linearly in opposite directions between a measuring position in which the first and second light transmitting apertures are in an overlapping relationship with respect to one another, and an illumination position in which the first and second light transmitting apertures are in a non-overlapping relationship with respect to one another and the illuminator is proximate the assay sample reservoir such that the illuminator causes luminescence of the assay sample;

supporting the assay sample vessel containing the assay sample;

operating the shutter assembly to cause the first and second shutter blades to reach and maintain the illumination position;

illuminating the assay sample to cause luminescence;

operating the shutter assembly to cause the first and second shutter blades to reach and maintain the measuring position; and measuring the luminescence.

12. The method of claim 11, wherein the sample analyzer further comprises:
a first toothed arm extending from the first shutter blade;
a second toothed arm extending from the second shutter blade; and
a motor having a gear disposed between, and meshed with, the first and second toothed arms such that rotation of the gear causes the first and second shutter blades to move linearly in opposite directions between the measuring position and the illumination position.

13. The method of claim 11, further comprising a flexible circuit with an LED illuminator thereon and attached to the first shutter blade.

14. The method of claim 11, wherein an analyte concentration in the assay sample is determined by measuring the luminescence at and for predetermined times and, using sample analyzer software, calculating the analyte concentration in the assay sample from the measured luminescence.

15. The method of claim 11, wherein the assay sample is contained in a disc shaped sample reservoir in the assay sample vessel.

16. The method of claim 11, wherein the detector is a photomultiplier tube.

17. The method of claim 11, wherein the sample analyzer further comprises a reflector permanently mounted proximate a side of the assay sample reservoir opposite the detector, aligned with and perpendicular to the optical axis, to reflect light from the illuminator back into the assay sample in an illumination mode and to reflect a portion of the luminescence back through the assay sample toward the detector in a measuring mode.

18. The method of claim 11, wherein the assay sample vessel includes a reflector on a side of the sample reservoir opposite the detector, aligned with and perpendicular to the optical axis, to reflect light from the illuminator back into the assay sample in an illumination mode and to reflect a portion of the luminescence back through the assay sample toward the detector in a measuring mode.

19. A shutter assembly, comprising:
a first shutter blade having a first toothed arm extending therefrom, a first light transmitting aperture therein, and an illuminator thereon;
a second shutter blade positioned adjacent and parallel to the first shutter blade, the second shutter blade having a second toothed arm extending therefrom and a second light transmitting aperture therein, the first and second shutter blades supported to allow parallel linear motion; and
a motor having a gear disposed between, and meshed with, the first and second toothed arms such that rotation of the gear causes the first and second shutter blades to move linearly in opposite directions between an open measuring position in which the first and second light transmitting apertures are in an overlapping relationship with respect to one another, and a closed illumination position in which the first and second light transmitting apertures are in a non-overlapping relationship with respect to one another and the illuminator is positioned to illuminate away from the second shutter blade.

* * * * *